United States Patent [19]

Kleemann et al.

[11] 4,335,126

[45] Jun. 15, 1982

[54] 1-[3-(3,4,5-TRIMETHOXYPHENOXY)-2-HYDROXY-PROPYL]-4-ARYL-PIPERAZINE-DERIVATIVES HAVING PHARMACEUTICAL ACTIVITY

[75] Inventors: Axel Kleemann, Hanau; Vladimir Jakovlev, Maintal; Klaus Thiemer, Hanau; Jürgen Engel, Alzenau, all of Fed. Rep. of Germany

[73] Assignee: Degussa Aktiengesellschaft, Frankfurt, Fed. Rep. of Germany

[21] Appl. No.: 193,482

[22] Filed: Oct. 3, 1980

Related U.S. Application Data

[63] Continuation-in-part of Ser. No. 891,382, Mar. 29, 1978, abandoned.

[30] Foreign Application Priority Data

Apr. 4, 1977 [GB] United Kingdom ............... 10100/77

[51] Int. Cl.³ .................. A61K 31/495; C07D 295/08
[52] U.S. Cl. ..................................... 424/250; 544/394
[58] Field of Search ................. 544/394, 391; 424/250

[56] References Cited

FOREIGN PATENT DOCUMENTS 2814168 10/1978 Fed. Rep. of Germany ...... 544/394

Primary Examiner—Anton H. Sutto

Attorney, Agent, or Firm—Cushman, Darby & Cushman

[57] ABSTRACT

There are prepared compounds corresponding to the general formula

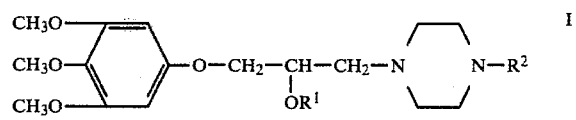

in which $R^1$ is a hydrogen atom, a $C_2$ to $C_6$-alkanoyl group, a $C_3$ to $C_6$-alkenoyl group, a $C_3$ to $C_6$-cycloalkyl carbonyl group, a benzoyl group, an alkoxybenzoyl group, a nicotinoyl group, a thienyl carbonyl group, a furyl carbonyl group, a phenylacetyl group or a $C_1$ to $C_4$-alkoxyphenyl acetyl group and $R^2$ represents a phenyl, naphthyl or pyridyl group or such group substituted by the groups $R^3$ and $R^4$, the groups $R^3$ and $R^4$, which may be the same or different, each representing hydrogen, hydroxyl, fluorine, chlorine, bromine, a nitro group, a trifluoromethyl group, a $C_1$ to $C_6$-alkyl group, a $C_1$ to $C_6$-alkoxy group, a $C_1$ to $C_6$-alkyl thio group, a $C_1$ to $C_6$-alkyl sulphonyl group, a $C_2$ to $C_6$-alkanoyl group, an amino group, an acylamino group or an acyloxy group in which the acyl is of the type defined in respect to $R^1$, and their salts. The compounds are pharmacodynamically active.

43 Claims, No Drawings

1-[3-(3,4,5-TRIMETHOXYPHENOXY)-2-HYDROXY-PROPYL]-4-ARYL-PIPERAZINE-DERIVATIVES HAVING PHARMACEUTICAL ACTIVITY

CROSS-REFERENCE TO RELATED APPLICATION

This application is a continuation-in-part of application Ser. No. 891,382, filed Mar. 29, 1978 now abandoned.

BACKGROUND OF THE INVENTION

This invention relates to new 1-[3-(3,4,5-trimethoxyhenoxy)-2-hydroxypropyl]-4-aryl-piperazine derivatives and to a process for their production.

Witte German Offenlegungsschrift No. 2,235,597 describes blood-pressure-reducing compounds corresponding to the general formula

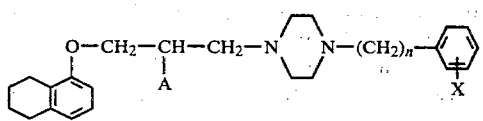

in which A is a hydrogen atom or a hydroxyl group, X is a hydrogen or a halogen atom, an alkyl, alkoxy, alkylthio, trifluoromethyl hydroxy, nitro, amino, acylamino or alkylsulphonylamino group, and n is the number 0, 1 or 2, and their salts.

de Stevens U.S. Pat. No. 3,211,735 discloses on col. 11–12 Compound 2

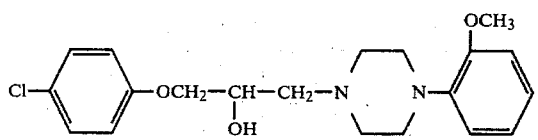

and on column 11–12, Compound 12

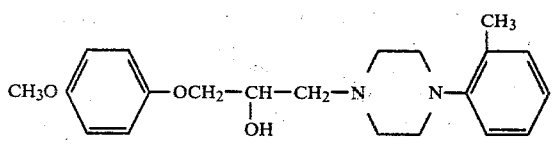

de Stevens states that its compounds have anti-inflammatory, antihypertension and adrenolytic properties, col. 3, lines 23–25 and also lines 26–48.

SUMMARY OF THE INVENTION

The present invention relates to new compounds corresponding to the general formula

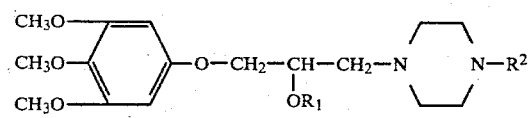

in which $R^1$ is a hydrogen atom, a $C_2$ to $C_6$-alkanoyl group, a $C_3$ to $C_6$-alkenoyl group, a $C_3$ to $C_6$-cycloalkyl carbonyl group, a benzoyl group, an alkoxybenzoyl group, a nicotinoyl group, a thienyl carbonyl group, a furyl carbonyl group, a phenyl acetyl group or a $C_1$ to $C_4$-alkoxy phenyl acetyl group and $R^2$ represents a phenyl, naphthyl or pyridyl group optionally substituted by the radicals $R^3$ and $R^4$, the radicals $R^3$ and $R^4$ which may be the same or different, each representing hydrogen hydroxyl, fluorine, chlorine, bromine, a nitro group, a trifluoromethyl group, a $C_1$ to $C_6$-alkyl group, a $C_1$ to $C_6$-alkoxy group, a $C_1$ to $C_6$-alkylthio group, a $C_1$ to $C_6$-alkyl sulphonyl group, a $C_2$ to $C_6$-alkanoyl group, an amino group, an acylamino group or an acyloxy group; in each of the last two groups the acyl is of the type defined in respect of $R^1$, and to the salts of these compounds, preferably the pharmaceutically acceptable salts.

The alkanoyl alkenyol radicals may be linear or branched. The alkanoyl radicals consist in particular of 2, 3 or 4 carbon atoms, e.g., acetyl, propionyl or butyryl, whilst the alkenoyl group consists in particular of 3, 4 or 5 carbon atoms, e.g., acryloyl, methacryloyl, crotonoyl, ethacryloyl. The thienyl and furyl carbonyl radicals may be respectively the corresponding thienyl-(2)- or thienyl-(3)-carbonyl radical and the furyl-(2)- or furyl-(3)-carbonyl radical. In the case of the $C_1$ to $C_4$-alkoxy phenyl acetyl radical or the $C_1$ to $C_4$-alkoxyl-benzoyl radical, the phenyl radical may be substituted once, twice or three times by the lower alkoxy groups. The preferred alkoxy group is the methoxy group.

The alkyl, alkoxy, alkyl-thio and alkyl sulphonyl radicals may each be linear or branched in regard to the respective alkyl groups. Examples of these radicals are methyl, ethyl, propyl, isopropyl, butyl, sec. butyl, hexyl, methoxy, ethoxy, propoxy, isopropoxy, butoxy, tert.-butoxy, hexoxy, methylthio, ethylthio, propylthio butylthio, hexylthio, methyl sulphonyl, ethyl sulphonyl, propyl sulphonyl, butyl sulphonyl, hexyl sulphonyl. Examples of the acylamino group are the propionolyamino group, capronoylamino group, acetamino group and benzoylamino group. Where $R^2$ is a naphthyl radical, it may be the naphthyl-(1)- or naphthyl-(2)-radical, this naphthyl radical optionally being substituted in either or both rings by the radicals $R^3$ and $R^4$. However, the naphthyl ring is preferably substituted in the ring which is not attached to the piperazine ring. Where $R^2$ is a pyridyl ring, this ring may be attached to the piperazine ring in the 2-, 3- or 4-position.

$R^1$ is preferably hydrogen or an alkanoyl group having 2, 3 or 4 carbon atoms.

In case $R^2$ is a phenyl or pyridyl group the substituents $R^3$ and/or $R^4$ are preferably adjacent to the carbon atom coupling $R^2$ with the piperazine ring.

Preferably $R^1$ is hydrogen and $R^2$ is a $C_1$–$C_4$-alkoxyphenyl group (for example, methoxyphenyl, ethoxyphenyl, propoxyphenyl, isopropoxyphenyl, butoxyphenyl), a hydroxyphenyl group, an aminophenyl group, a $C_2$–$C_4$-alkanoylaminophenyl group (for example, acetylaminophenyl, propionylaminophenyl, butyrylaminophenyl), or a $C_2$–$C_4$-alkanoxyloxyphenyl group (for example, acetoxyphenyl, propionyloxyphenyl butyryloxyphenyl) wherein these substituents are in the o- or p-position, particularly the o-position.

The new compounds are pharmadocyamically active and show, for example, a pronounced antiaggressive action together with neuroleptic properties, anticonvulsive and hypnotic effects being in evidence to a very limited extent only, if at all. In addition, the new compounds show fever-reducing and oedema-inhibiting effects. Accordingly, an object of the invention is to provide compounds with favorable pharmacodynamic properties which may be used as medicaments.

By contrast, the [3-(5,6,7,8-tetrahydronaphthyl-(1)-oxypropyl]-piperazine derivatives described in German Offenlegungsschrift No. 2,235,597 show blood-pressure-reducing and hence antihypertensive properties. Unlike these derivatives, the compounds according to the invention show very little, if any, blood-pressure-reducing activity.

The compounds according to the invention may be produced by reacting a compound corresponding to the formula

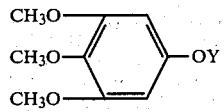
II with a compound corresponding to the formula

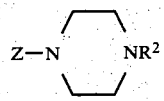
III in which Y and Z are different from one another and one represents hydrogen, whilst the other represents the the group —$CH_2$—$CH(OR^1)$—$CH_2$—V where V represents chlorine, bromine or iodine or, where $R^1$ is a hydrogen atom, may also form an ethylene oxide ring together with this hydroxy group, and optionally reducing one or two nitro groups to amino groups and/or acylating the compounds obtained with an acid or acid derivative corresponding to the radical $R^1$.

The process for producing the compounds according to the invention may be carried out in the presence or absence of a solvent at a temperature in the range from 20° to 200° C. and preferably at a temperature in the range from 50° to 150° C. Suitable solvents or dispersants are, for example, aromatic hdyrocarbons such as, for example, benzene, toluene, xylene; aliphatic ketones such as, for example, acetone, methylethyl ketone; halogenated hydrocarbons such as, for example, chloroform, carbon tetrachloride, chlorobenzene, methylene chloride; aliphatic ethers such as, for example, butyl ether; cyclic ethers such as, for example, tetrahydrofuran, dioxane; sulphoxides such as, for example, dimethyl sulphoxide; tertiary acid amides such as, for example, dimethyl formamide, N-methyl pyrrolidone; aliphatic alcohols, such as methanol, ethanol, isopropanol, amyl alcohol, tert.-butanol; cycloaliphatic hydrocarbons, such as cyclohexane and the like. Mixtures of the above-mentioned solvents may also be used. In many cases, the reaction is carried out at the reflux temperature optionally followed by treatment with acids of the formula $R^1OH$, in which $R^1$ has any of the meanings defined except hydrogen, or by treatment with the corresponding reactive acid derivatives.

Corresponding acid derivatives are, in particular, compounds corresponding to the formula

 $R^1W$
IV in which W represents chlorine, bromine or iodine, the group —N≡N, a group of the formula —OR', —SR' or a group of the formula —$OSO_3H$, —O—$PO(OH)_2$, —$OP(OR')_2$, —O—$As(OR')_2$ or —OCO—R". In these groups, R' represents an alkyl radical, e.g., methyl, ethyl or butyl or even, in the case of —OR' and —SR', for example a phenyl radical, a p-nitrophenyl radical, a cyanomethyl radical or a carboxymethyl radical; R" may be a linear or branched alkyl radical, e.g., methyl, ethyl, isopropyl, an alkoxy radical, e.g., methoxy, ethoxy, a phenoxy radical, a carbobenzoxy radical or even the radical $R^1$. Aliphatic $C_2$ to $C_6$-ketenes, e.g., ketene itself, may also be used as acylating agents. Acid derivatives of formula IV in which W is chlorine or bromine represent particularly appropriate acylating agents, e.g., acetyl chloride, acetyl bromide, propionyl chloride, acryloyl chloride, benzoyl chloride. Where R' and R" represent alkyl radicals or alkoxy radicals, these radicals are preferably of low molecular weight and consist of 1 to 6 carbon atoms, e.g., methyl, hexyl, methoxy, hexoxy. of the solvent or dispersant used. In general, the reaction components are reacted in molar quantities. In some cases, however, it can be of advantage to use the compound of formula III in excess (for example 0.5 mol) where Z is a hydrogen atom. The reaction may also be carried out in the presence of an acid-binding agent, such as an alkali metal carbonate (potash, soda), an alkali metal hydroxide, e.g., sodium hydroxide or potassium hydroxide or a tertiary amine (for example triethylamine). This applies in particular when compounds in which V is a halogen atom are used.

Where a compound of formula II in which Y is a hydrogen atom is used as the starting substance, this compound may also be used in the form of a metal salt, more especially an alkali metal salt (for example the sodium or potassium salt). This applies in particular when, in the other reaction component III, the symbol V in the group Z, which is —$CH_2$—$CH(OR^1)$—$CH_2V$, is a halogen atom.

For carrying out the reaction, the ethylene oxide starting compound may even be replaced by the corresponding halohydrin (e.g., chlorohydrin) or by a mixture of these two compounds (crude synthesis product).

In the products obtained, the amino and/or hydroxy groups present and also the secondary hydroxy group in the central position (introduction of the $R^1$-acyl radical) can be acylated.

The acylation step may be carried out, for example, in an inert solvent or suspending agent such as water, a lower aliphatic alcohol, e.g., methanol, ethanol, isopropanol, a lower aliphatic ketone, e.g., acetone, methyl ethyl ketone, dioxane, dimethyl formamide, benzene or toluene, at a temperature of from 0° to 200° C. The acylation step is optionally carried out in the presence of an acid-binding agent, such as an alkali metal hydroxide, e.g., sodium hydroxide, potassium hydroxide, an alkali metal carbonate (potassium carbonate), an alkali metal hydrogen carbonate, e.g. sodium bicarbonate, an alkali metal acetate, e.g., sodium acetate, an alkaline earth metal carbonate, e.g., calcium carbonate, a tertiary amine (for example, trialkylamine, e.g., triethylamine, pyridine) or an alkali metal alcoholate, e.g. (sodium ethylate).

It is also possible initially to convert the groups to be acylated (hydroxy group, amino group) in the compound to be reacted into the corresponding alkali metal compound by reacting them with an alkali metal, an alkali metal hydride or an alkali metal amide (especially sodium or a sodium compound, e.g., sodamide) at a temperature of from 0° to 150° C. in an inert solvent, such as dioxane, dimethyl formamide, benzene or toluene, and subsequently adding the acylating agent.

In cases where the free acid with the formula $R^1OH$ is used, it has to be activated by the presence of a condensation agent, such as dicyclohexyl carbodiimide, a sulphurous acid-bis-alkyl amide (for example $SO[N(CH_3)_2]_2$), N,N'-carbonyl diimidazole and so on (Organic Reactions, Vol. 12, 1962, pages 205 and 239).

Instead of using the acylating agents mentioned above, it is also possible to use other chemically equivalent agents commonly encountered in chemistry (cf. for example L. F. and Mary Fieser "Reagents for Organic Synthesis", John Wiley and Sons, Inc., New York, 1967, Vol. 1, pages 1303-4 and Vol. 2, page 471). Any acyl groups present in the compounds obtained may of course also be split off again in known manner, for example with aqueous alkali or alcoholic alkali metal hydroxide (for example, methanolic KOH) or possibly even with mineral acids, such as hydrochloric acid or sulphuric acid, in alcoholic or aqueous-alcoholic solution at a temperature in the range from 20° C. to 100° C.

For the reduction of one or even two nitro groups there is particularly employed catalytic hydrogen. As catalysts there can be used, for example, Raney-nickel, noble metals such as palladium and platinum as well as their compounds, with or without carriers, as for example barium sulphate, calcium sulphate, etc. It is recommended to carry out the hydrogenation of the nitro groups at temperatures between 20° and 80° C. and a pressure of approximately 5-50 atmospheres absolute in a solvent, for example, an alcohol, e.g., methyl alcohol, ethyl alcohol or isopropyl alcohol, dioxane, tetrahydrofuran, etc. In many cases, it is advantageous for the subsequent isolation of the reduced compounds to add at the beginning to the hydrogenating mixture a drying agent such as anhydrous sodium sulphate or magnesium sulphate.

However, the reaction can also be carried out with nascent hydrogen, for example, zinc/hydrochloric acid, tin/hydrochloric acid, iron/hydrochloric acid or with salts of hydrogen sulphide and alcohol/water at about 70° to 120° C. or with activated aluminum in hydrated ether at 20° to 40° C. or with tin II chloride/hydrochloric acid.

The compounds according to the invention are generally obtained in the form of racemates. The optically active antipodes are obtained either by using optically active starting materials or by racemate splitting via the salts of optically active acids such as, for example L-(+)-tartaric acid, D-(−)-tartaric acid, (+)-O,O'-dibenzoyl-D-tartaric acid, (−)-O,O'-dibenzoyl-L-tartaric acid, (−)-O,O'-di-p-toluoyl-L-tartaric acid, (+)-O,O'-di-p-toluoyl-D-tartaric acid, (+)-camphor-10-sulphonic acid and others.

The compounds corresponding to general formula I may be converted into their salts by known methods. Suitable anions for these salts are the known and therapeutically usable acid radicals. Examples for acids such as these are $H_2SO_4$, phosphoric acid, hydrohalic acids, e.g., hydrochloric acid and hydrobromic acid, ethylene diamine tetraacetic acid, sulphamic acid, benzene sulphonic acid, p-toluene sulphonic acid, camphor sulphonic acid, methane sulphonic acid, guaiazulene sulphonic acid, maleic acid, fumaric acid, succinic acid, tartaric acid, lactic acid, ascorbic acid, glycolic acid, salicyclic acid, acetic acid, propionic acid, gluconic acid, benzoic acid, citric acid, acetaminoacetic acid, hydroxy ethane sulphonic acid.

The free bases may in turn be produced from the salts of the compounds in known manner, for example by treating a solution in an organic solvent, such as an alcohol (methanol), with soda or sodium hydroxide.

In addition to the compounds mentioned in the working examples, other compounds of the invention within formula I include, for example, the following

| $R^1$ | $R^2$ |
|---|---|
| H | 2,4-dihydroxyphenyl |
| H | 2,6-dichlorophenyl |
| H | 2,4-dinitrophenyl |
| H | 2-methyl-4-chlorophenyl |
| H | 2,4-di(trifluoromethyl)phenyl |
| H | 4-ethylphenyl |
| H | 2-sec. butylphenyl |
| H | 4-hexylphenyl |
| H | 4-propionylphenyl |
| H | 2-butyrylphenyl |
| H | 2-hexanoylphenyl |
| H | 4-butoxyphenyl |
| H | 2,4-dimethoxyphenyl |
| H | 2,4-diaminophenyl |
| H | 2-methyl-4-aminophenyl |
| H | 4-ethylmercaptophenyl |
| H | 2-butylmercaptophenyl |
| H | 4-hexylmercaptophenyl |
| H | 2-propionamidophenyl |
| H | 2-butyramidophenyl |
| H | 2-capronamidophenyl |
| H | 2-methylsulphonylphenyl |
| H | 4-ethylsulphonylphenyl |
| H | 2-butylsulphonylphenyl |
| H | 2-hexylsulphonylphenyl |
| H | 2-acetyloxyphenyl |
| H | 2-propionyloxyphenyl |
| H | 4-acetyloxyphenyl |
| H | 2-butyryloxyphenyl |
| H | 2-hexanoyloxyphenyl |
| H | 5-hydroxynaphth-(1)-yl |
| H | 5-methylnapth-(1)-yl |
| H | 3-methylpyrid-(2)-yl |
| H | 3-nitropyrid-(2)-yl |
| H | 3-fluoropyrid-(2)-yl |
| H | 3-chloropyrid-(2)-yl |
| H | 4-methylpyrid-(2)-yl |
| H | 3,5-dimethylpyrid-(2)-yl |
| acetyl | phenyl |
| acetyl | 2-methoxyphenyl |
| acetyl | 2-chlorophenyl |
| acetyl | 2-aminophenyl |
| acetyl | 3-methoxyphenyl |
| propionyl | phenyl |
| propionyl | 2-trifluoromethylphenyl |
| butyryl | 4-acetylphenyl |
| acetyl | naphth-(1)-yl |
| acetyl | pyrid-(2)-yl |
| hexanoyl | phenyl |
| acryloyl | phenyl |
| acryloyl | 5-methoxyphenyl |
| methacryloyl | phenyl |
| crotonoyl | phenyl |
| cyclopropylcarbonyl | phenyl |
| cyclohexanoyl | phenyl |
| benzoyl | phenyl |
| benzoyl | 2-methylphenyl |
| benzoyl | 2,4-dimethoxyphenyl |
| thienyloyl | 2-aminophenyl |
| furylcarbonyl | phenyl |
| phenylacetyl | 2-ethoxyphenyl |
| 2-methoxyphenylacetyl | 2-methoxyphenyl |
| 2-ethoxyphenylacetyl | phenyl |
| 2-butoxyphenylacetyl | 2-hydroxyphenyl |
| 2-methoxybenzoyl | 2-methoxyphenyl |
| 3-ethoxybenzoyl | phenyl |
| 2-butoxybenzoyl | 3-fluorophenyl |

The compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared in known manner with the usual pharmaceutical excipients, assistants, carriers and diluents.

As carriers and assistants, for example, are those recommended in the following literature as adjuvants for pharmacy, cosmetic and related fields such as in Ullmann's Encyklopädie der technischen Chemie, Vol. 4 (1953), pages 1 to 39; Journal of Pharmaceutical Sciences 52 (1963), pages 918 et seq.; N. v. Czetsch-Lindenwald, Hilfsstoffe für Pharmazie und angrenzende Gebiete; Pharm. Ind. 2 (1961), pages 72 et seq.; Dr. H. P. Fiedler, Lexicon der Hilftstoffe für Pharmazie, Kosmetik und angrenzende Gebiete, Cantor Kg. Aulendorf i. Württ (1971).

Examples of such materials include gelatin, natural sugars such as sucrose or lactose, lecithin, pectin, starch (for example cornstarch), alginic aicd, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, corn oil, wheat germ oil, sunflower seed oil, cod-liver oil), mono-, di- and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetin, diacetin, glyceryl monostearate, glyceryl distearate, glyceryl monopalmitate, paraffins and the like.

In the production of the preparations there can be used known and customary solution aids or emulsifiers. As solution aids and emulsifiers there can be used, for example, polyvinyl pyrrolidone, sorbitan fatty acid esters such as sorbitan trioleate, lecithin, gum acadia, gum tragacanth, polyoxyethylated sorbitan monoleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Friedler, supra, pages 191–195).

Furthermore, there can be added preservatives, stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium metal bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for example, by means of a colloid mill or ball mill), wherein the operation is generally carried out at temperatures between 20° and 80° C., preferably 20° to 50° C.

The application of active material or drug can take place on the skin or mucous membrane or internally, for example, orally, parenterally, pulmonarily, rectally, nasally, vaginally, perlingually, intravenously, intraarterially, intracardially, intramuscularly, intraperitoneally, intracutaneously or subcutaneously.

The addition of other medicines is also possible or favorable.

The compounds of the invention in the fighting test, mouse (R. E. Tedeschi and coworkers, J. Pharmacol. Exp. Therap., Vol. 125, page 28 (1959) or in the amphetamine group toxicity test, mouse, H. Fujimori and coworkers, J. Pharmacol. Exp. Therap., Vol. 148, page 151 (1965) showed a good anxiolytic-anti-aggressive or amphetamine-antagonistic (neuroleptic property) activity.

For example in the above-mentioned test methods at a dosage of 2.0 mg/kg body weight mouse there occurred the anxiolytic-anti-aggressive and amphetamine-antagonistic activity. This tranquilizing-neuroleptic activity is comparable with the activity of the known medicines Diazepam and Chlorpromazin.

The lowest clearly effective dosage in the above-mentioned animal experiments is, for example, 0.1 mg/kg orally; 0.01 mg/kg intravenously.

As the general dosage range for the above-mentioned activities (animal experiments as above), there can be used, for example, 0.1 to 20 mg/kg orally, particularly 1.0 to 10 mg/kg, 0.01 to 5.0 mg/kg intravenously, particularly 0.1 to 1.0 mg/kg.

The compounds of the invention are indicated for use in excitement, internal tension, anxiety, psychoneurotic disturbances, disturbances of sleep, psychoses, depression conditions.

The pharmaceutical preparations generally contain between 0.1 to 50 mg of the active component or components of the invention.

The compounds can be delivered in the form of tablets, capsules, pills, dragees, plugs, salves, gels, suppositories, ointments, jellies, creams, powders, dusts, aerosols or in liquid form. As liquid forms there can be used for example oily or alcoholic or aqueous solutions as well as suspension and emulsions. The preferred forms of use are tablets which contain between 0.5 and 30 mg or solutions which contain between 0.1 and 5% of active material.

In individual doses, the amount of active component of the invention can be used for example in an amount of:

a. in oral dispensation between 0.1 and 50 mg;
b. in parenteral dispensation (for example, intravenously, intramuscularly) between 0.01 and 10 mg;
c. in dispensation rectally or vaginally between 0.2 and 200 mg.

For example, there is recommended the use of 1 to 3 tablets containing 0.5 to 20 mg of active ingredient 3 times daily or for example, intravenously the injection 1 to 6 times daily of a 1 to 10 ml ampoule containing 0.01 to 5.0 mg of active substance. In oral preparations the minimum daily dosage for example is 10 mg; the maximum daily dosage in oral administration should not be over 10 grams.

The dosages in each case are based on the free base.

In veterinary medicine the compounds of the invention can be used in treating dogs and cats. The individual dosages in general orally are between approximately 0.1 and 20 mg/kg body weight; the parenteral dosage approximately between 0.01 and 5.0 mg/kg body weight.

For the treatment of horses and cattle, the individual oral dosages are generally between about 0.1 and 20 mg/kg; the individual parenteral dosages between about 0.01 and 20 mg/kg body weight.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is between 100 mg/kg and 5000 mg/kg, in some cases even above 5000 mg/kg.

The drugs can be used in human medicine, in veterinary medicine as well as in agriculture alone or in admixture with other pharmacologically active materials. The salts can be used as catalysts to cure melamine-formaldehyde resins.

Unless otherwise indicated, all parts and percentages are by weight.

The compositions can comprise, consist essentially of or consist of the materials set forth.

The methods can comprise, consist essentially of or consist of the steps set forth with the materials shown.

Starting compounds of formula III, in which Z represents the group $-CH_2-CH(OH)-CH_2-V$, may be obtained for example in the usual way by reacting epichlorohydrin or epibromohydrin with the corresponding piperazine, which contains the radical $R^2$ in the 4-position, at 10° C. in an alcohol, preferably methanol, with approximately 5% of water added. The reaction time amounts for example to 30 minutes. The reaction mixture is then heated to 30° to 40° C. and stirred for 5 hours.

The ratio of piperazine to the hydrin amounts, for example, to from 1:1 to 1:5 and preferably to from 1:1 to 1:2. The water content may be from 1 to 10% and is preferably from 2 to 6%.

In the compounds thus obtained, the radical $R^1$ may be introduced by acylation with a compound $R^1W$ under the conditions specified above. $R^1$ may also be introduced in the same way into starting compounds of formula II in which Y represents the group $-CH_2-CH(OH)-CH_2-V$.

The other starting compounds are known.

DESCRIPTION OF THE PREFERRED EMBODIMENTS

Example 1

(±)-1-[3-(3,4,5-trimethoxyphenoxy)-2-hydroxypropyl]-4-(2-methoxyphenyl)-piperazine (a) 12 g (0.05 mole) of 3,4,5-trimethoxyphenoxy glycidyl ether and 9.6 g (0.05 mole) of 1-(2-methoxyphenyl)-piperazine are boiled under reflux for 5 hours in 100 ml of isopropanol. Most of the solvent is then distilled off, the residue is treated with excess isopropanolic HCl and the dihydrochloride of the 1-[3-(3,4,5-trimethoxyphenoxy)-2-hydroxypropyl]-4-(2-methoxyphenyl)-piperazine is precipitated by the addition of diethyl ether, giving 18.4 g (73% of the theoretical) of a colorless crystalline substance. M.p. of the dihydrochloride: 196°–197° C.

The 3,4,5-trimethoxyphenoxy glycidyl ether is produced for example as follows:

In a suitable reaction vessel fitted with an attachment for the azeotropic separation of water, 18.4 g (0.1 mole) of 3,4,5-trimethoxyphenol are brought to the boil with 37 g (0.4 mole) of epichlorohydrin, followed by the dropwise addition over a period of 30 minutes of 10 g (0.1 mole) of 40% sodium hydroxide, the water being simultaneously removed azeotropically from the circuit. After the sodium hydroxide has been added, the mixture is left to react for 1 hour at boiling temperature, subsequently diluted with approximately 100 ml of toluene and the NaCl precipitated is filtered off. The filtrate is fractionated first under normal pressure and then in vacuo. The 3,4,5-trimethoxyphenoxy glycidyl ether is obtained as a colorless oil at $b.p._{1.0}=175°-180°$ C. Yield 19.2 g, corresponding to 80% of the theoretical, based on trimethoxyphenol.

The process for producing the end product may also be carried out as follows:

0.05 mole of sodium-(3,4,5,-trimethoxy)-phenolate and 0.05 mole of 1-(3-chloro-2-hydroxypropyl)-4-(2-methoxyphenyl)-piperazine (produced by reacting 1-(2-methoxyphenyl)-piperazine with epichlorohydrin) are boiled under reflux for 8 hours in 50 ml of dioxane. After cooling, the NaCl precipitated is filtered off and the filtrate is concentrated. The residue is treated with isopropanolic hydrochloric acid and ether and the crystalline solid is recrystallized from methanol, giving 8.2 g (32% of the theoretical) of the above-mentioned compound in the form of its dihydrochloride melting at 194°–196° C.

Another way of carrying out the process is as follows:

A mixture of 0.05 mole of 3-(3,4,5,-trimethoxyphenoxy)-2-hydroxypropyl bromide, 0.05 mole of 1-(2-methoxyphenyl)-piperazine and 0.06 mole of triethylamine is boiled under reflux for 5 hours in 100 ml of toluene. The triethyl ammonium bromide precipitated is then filtered off and the filtrate is concentrated. The residue is taken up in a little isopropanol and the dihydrochloride of the above-mentioned compound is precipitated with isopropanolic hydrochloric acid and ether. Recrystallization from methanol gives 10.1 g of end product (40% of the theoretical) melting at 195°–197° C.

The compounds listed in Table 1 corresponding to the formula

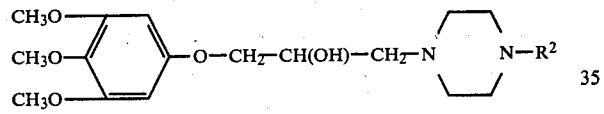

are obtained in the same way as described in the first paragraph of Example 1 from 0.05 mole of 3,4,5-trimethoxyphenoxy glycidyl ether and 0.05 mole of a compound corresponding to formula III:

Example 22

(±)-1-[3-(3,4,5-Trimethoxyphenoxy)-2-(nicotinoyloxy)-propyl]-4-(2-methoxyphenyl)-piperazine 13.0 g (0.03 mole) of (±)-1-[3-(3,4,5-trimethoxyphenoxy)-2-hydroxypropyl]-4-(2-methoxyphenyl)-piperazine and 3.34 g of triethylamine (0.003 mole) are dissolved in 80 ml of anhydrous benzene, followed by the addition over a period of 30 minutes of a solution of 4.67 g (0.033 mole) of nicotinic acid chloride in 50 ml of anhydrous benzene. After stirring for another 2 hours at room temperature, the mixture is finally heated for 1 hour to 70° to 80° C. After cooling, the mixture is repeatedly extracted by shaking with water, washed with aqueous NaHCO₃ and water and the benzene phase is dried with magnesium sulphate and concentrated. The solid residue was taken up in dioxane. After the addition of excess isopropanolic hydrochloric acid and ether, 13.0 g (67% of the theoretical) of the above-mentioned compound are obtained in the form of its trihydrochloride (colorless crystals). M.p. 187°–192° C. (decomposition).

Example 23

(±)-1-{3-[3,4,5-Trimethoxyphenoxy)-2-[(3,4,5-trimethoxy)-benzoyloxy]-propyl}-4-(2-methoxyphenyl)-piperazine (±)-1-[3-(3,4,5-Trimethoxyphenyl)-2-hydroxypropyl]-4-(2-methoxyphenyl)-piperazine is reacted with 3,4,5-trimethoxybenzoyl chloride in the presence of triethylamine as in Example 22. The reaction product is obtained in the form of the dihydrochloride melting at 193°–195° C. (decomposition). Yield: 38%.

Example 24

(±)-1-[3-(3,4,5-Trimethoxyphenoxy)-2-hydroxypropyl]-4-(2-acetamido-phenyl)-piperazine 4 g (±)-1-[3-(3,4,5-Trimethoxyphenoxy-2-hydroxyphenyl]-4-(2-amino-phenyl)-piperazine(monohydrochloride) are dissolved in 200 ml of dioxane and treated with 10 ml of triethylamine. Then there were dropped

TABLE 1

| Example No. | Starting component of formula III | R² in the above formula | Melting point °C. | Yield in % of the Theoretical |
|---|---|---|---|---|
| 2 | 1-phenyl piperazine | phenyl | 187–188** | 65 |
| 3 | 1-(4-fluorophenyl)-piperazine | 4-fluorophenyl | 202–203** | 74 |
| 4 | 1-(2-chlorophenyl)-piperazine | 2-chlorophenyl | 193–195* | 72 |
| 5 | 1-(3-chlorophenyl)-piperazine | 3-chlorophenyl | 172–173* | 68 |
| 6 | 1-(4-chlorophenyl)-piperazine | 4-chlorophenyl | 199–201** | 79 |
| 7 | 1-(3-methoxyphenyl)-piperazine | 3-methoxyphenyl | 202–204** | 82 |
| 8 | 1-(4-methoxyphenyl)-piperazine | 4-methoxyphenyl | 208–210** | 74 |
| 9 | 1-(2-ethoxyphenyl)-piperazine | 2-ethoxyphenyl | 198–200** (decomposition) | 64 |
| 10 | 1-(2-methylmercaptophenyl)-piperazine | 2-methylmercaptophenyl | 183–185* | 69 |
| 11 | 1-(2-methylphenyl)-piperazine | 2-methylphenyl | 198–199* | 54 |
| 12 | 1-(3-methylphenyl)-piperazine | 3-methylphenyl | 189–192** | 68 |
| 13 | 1-(3,4-dimethylphenyl)-piperazine | 3,4-dimethylphenyl | 186–188** | 80 |
| 14 | 1-(2,6-dimethylphenyl)-piperazine | 2,6-dimethylphenyl | 228–230* | 71 |
| 15 | 1-(4-acetylphenyl)-piperazine | 4-acetylphenyl | 137–138 (base) | 58 |
| 16 | 1-(2-trifluoromethylphenyl)-piperazine | 2-trifluoromethylphenyl | 205–206* | 52 |
| 17 | 1-(3-trifluoromethylphenyl)-piperazine | 3-trifluoromethylphenyl | 169–172** | 69 |
| 18 | 1-naphth-(1)-yl-piperazine | naphth-(1)-yl | 242–245* | 61 |
| 19 | 1-pyrid-(2)-yl-piperazine | pyrid-(2)-yl | 222–224** | 47 |
| 20 | 1-(2-hydroxyphenyl)-piperazine | 2-hydroxyphenyl | 131 (base) | 61 |
| 21 | 1-(2-nitrophenyl)-piperazine | 2-nitrophenyl | 198* | 55 |

*monohydrochloride
**dihydrochloride in with stirring at −5° C. 0.9 ml of acetyl chloride. After two hours of further reaction at room temperature, the solution is filtered at room temperature and the solvent removed reduced pressure. The desired compound is isolated by dry column chromatography on silica gel (elution material ether-acetic acid (1:1 by volume). Recrystallization takes place from acetone-ether. Yield: 50%, M.p. 128°–130° C.

As the less polar byproduct which can be made the main product by increase in the amount of acetyl chloride there is obtained (±)-1-[3-(3,4,5-Trimethoxyphenoxy)-2-acetoxy-propyl]-4-(2-acetamidophenyl)-piperazine. M.p. 54° C.

Example 25

(±)-1-[3-(3,4,5-Trimethoxyphenoxy)-2-hydroxy-propyl]-4-(2-aminophenyl)-piperazine 6 g (0124 mole) (±)-1-[3-(3,4,5-trimethoxyphenoxy)-2-hydroxy-propyl]-4-(2-nitro-phenyl)-piperazine are dissolved in 300 ml of methanol and hydrogenated in the presence of 0.5 g Pd-carbon (10%) at room temperature. After filtering off the catalyst and removal of the solvent in vacuo it is recrystallized from ethanol. Yield: 94%. M.p. of the monohydrochloride: 181°–183° C.

EXAMPLE OF RESOLUTION

Example 26

(±)-1-[3-(3,4,5-trimethoxyphenoxy)-2-hydroxypropyl]-4-(2-methoxyphenyl)-piperazine (base = compound 1a)
and
(−)-1-[3-(3,4,5-trimethoxyphenoxy)-2-hydroxypropyl]-4-(2-methoxyphenyl)-piperazine (base = compound 1b)

4.32 g (0.005 mole) of the racemic compound produced in accordance with Example 1 are dissolved in 80 ml of warm butylacetate, followed by the addition in portions with thorough stirring at 80° C. of 4.04 g (0.005 mole) of (−)-di-p-toluoyl-L-tartaric acid hydrate, the levorotatory diastereomeric salt pair actually being precipitated. After heating for 10 minutes to 110° C., the mixture is left to cool to 80° C. and the deposit is filtered off. The salt pair is recrystallized from acetone-dimethyl formamide-petrol ($[\alpha]_D^{20}$ −48.6°; 1% in dimethyl formamide), and is subsequently split by treatment with concentrated ammonia. The base is extracted with ether and the extract is concentrated. The solid residue is recrystallized from isopropanol: 1a-base colorless crystals, M.p. 103°–104° C.; $[\alpha]_D^{20}$ +7.2° (concentration 2% in $CH_3OH$). Dissolution of the base in methanol, followed by the addition of isopropanolic hydrochloric acid and ether gives the dihydrochloride of compound 1a in the form of colorless crystals melting at 189°–193° C.; $[\alpha]_D^{20}$ −11.4° (concentration = 2% in $CH_3OH$).

The filtrate obtained after precipitation of the salt pair, which contains the dextrorotatory diastereomeric salt pair, is concentrated in a rotary evaporator, the viscous residue is suspended in water, concentrated ammonia is added and the base extracted with ether. The etheral solution is dried and concentrated and the solid residue is recrystallized from isopropanol: 1b-base, colorless crystals, m.p. 100°–101° C.; $[\alpha]_D^{20}$ −5.8° (concentration—2% in $CH_3OH$).

Dissolution of the base in methanol and treatment with isopropanolic hydrochloric acid and ether gives the dihydrochloride of compound 1b in the form of colorless crystals melting at 182°–187° C.; $[\alpha]_D^{20}$ +11.0° (concentration = 2% in $CH_3OH$).

EXAMPLES OF PHARMACEUTICAL PREPARATIONS

Example 27

Injection Solution

For a mixture of 100 liters there are needed:

| Compound according to Example 1 | | |
|---|---|---|
| (dihydrochloride) | 0.25 | kg |
| Sodium chloride | 0.775 | kg |
| Water for purpose of injection | 98.975 | kg |
| | 100.00 | kg |

Production:

The active material together with sodium chloride is dissolved with stirring in the water for purpose of injection. The solution is filtered and is filled into 2 ml ampoules of colorless glass. The ampoules after being closed by melting are sterilized for 20 minutes at 120° C. in superheated steam.

Example 28

Suppositories

Production:

5 g of the compound of Example 7 (dihydrochloride) is worked into 1995 g of molten suppository composition (for example, hard fat DAB 7, a mixture of mono-, di- and triglycerides of saturated fatty acids $C_{12}H_{24}O_2$ to $C_{18}H_{36}O_2$) and in known manner poured out in forms for 2.0 g of suppositories.

1 suppository contains 5 mg of active material.

Example 29

Capsules

To prepare 100,000 capsules there are required the following raw materials:

| Compound according to | | |
|---|---|---|
| Example 7 (dihydrochloride) | 0.125 | kg |
| Lactose | 7.200 | kg |
| Microcrystalline cellulose | 4.800 | kg |
| Magnesium stearate | 0.375 | kg |
| | 12.500 | kg |

To produce gelatin capsules (size 4) which are necessary for production of the capsule composition the previously set forth raw materials are passed through a sieve having a mesh width of 1.5 mm and then mixed for 1 hour at 10 revolutions per minute in a Turbula mixer. This composition is called the capsule filling composition.

This capsule filling composition is filled into gelatin capsules of size 2. Amount of filling per capsule: 125 mg.

Example 30

(±)-1-[3-(3,4,5-Trimethoxy-phenoxy)-2-hydroxy-propyl]-4-(2-acetoxy-phenyl)-piperazine

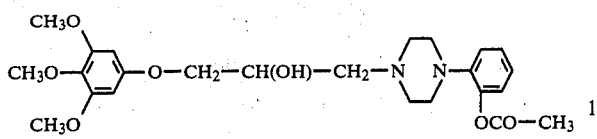

0.03 mole of 1-(2-acetoxy-phenyl)-piperazine (crude product) and 7.2 grams (0.03 mole) of 3,4,5-trimethoxy-phenoxy-glycidyl ether were heated in 150 ml of isopropanol under reflux until the reaction was complete according to thin layer chromatography control. After distilling off the solvent through treatment with isopropanolic hydrochloric acid there was obtained the hydrochloride and it was purified by recrystallization from isopropanol, M.P. 189°–191° C. Yield: 18%.

The 1-(2-acetoxy-phenyl)-piperazine starting material was obtained as follows:

192.8 grams (1 mole) of 2-methoxyphenyl-piperazine, 130 ml (1.1 moles) of benzyl chloride and 150 grams (1.10 moles) of potassium carbonate were heated in 800 ml of xylene under reflux until the reaction was complete according to DC control (control through thin layer chromatography). The product was filtered, the solvent removed in a vacuum and converted into the hydrochloride in the usual manner with isopropanolic hydrochloric acid. (Yield: 70%).

60 grams (0.2 mole) of the thus obtained hydrochloride were heated in 800 ml of 63% aqueous hydrobromic acid under reflux, until the splitting off of the ether was complete (DC control). Then the solvent was removed in a vacuum and the crystalline residue obtained washed with ether (Yield: 70%). The free base was set free in the usual way from the dihydrobromide with dilute aqueous ammonia.

10 grams (0.09 mole) of the thus obtained free base and 15 ml of triethylamine in 50 ml of dioxane were cooled to 50° C. and treated with 0.032 mole of acetyl chloride dropwise at a temperature of at most 10° C. After stirring for one hour at 10° C. the precipitated triethylamine hydrocloride was removed with suction and the solvent distilled off in a vacuum. Without further purification the benzyl group in the oily free base obtained was hydrogenated off as follows: 0.04 mole of the free base was dissolved in 150 ml of methanol and hydrogenated in the presence of 2 grams of Pd/C 10% at 50° C. under 5 bar. After the take up of hydrogen the catalyst was filtered off and the solvent removed in a vacuum. The 1-(2-acetoxy-phenyl)-piperazine thus obtained can be further reacted directly without additional purification.

In an analogous manner to Example 30, 3,4,5-trimethoxyphenoxy-glycidyl ether was reacted with 0.03 mole of the corresponding 1-(2-acyloxy-phenyl)-piperazine compound. The starting piperazine compound was obtained in each case in an analogous manner to the starting compound of Example 30 wherein in the acylation step in place of acetyl chloride in each case the corresponding other acid chloride (benzoyl chloride, cyclohexane carboxylic acid chloride) was used.

EXAMPLE 31

(±)-1-[3-(3,4,5-Trimethoxy-phenoxy)-2-acetoxy-propyl]-4-(2-methoxy-phenyl)-piperazine

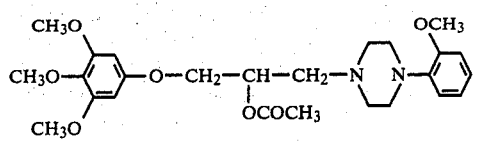

10 grams (0.023 mole) of (±)-1-[3-(3,4,5-Trimethoxy-phenoxy)-2-hydroxy-propyl]-4-(2-methoxy-phenyl)-piperazine were suspended in 100 ml of xylene. There were added thereto 10 ml of triethylamine and subsequently there were slowly dropped in 9 ml of acetyl chloride at room temperature. The solution was left at room temperature for 2 hours. Subsequently the triethylamine hydrochloride was filtered off and the solvent distilled off in a vacuum. The crude product obtained was purified by dry column chromatograph on silica gel (elution agent chloroform/methanol 98:2). The hydrochloride was obtained in the usual manner by treatment with isopropanolic hydrochloric acid and recrystallized from isopropanol. M.P. of the hydrochloride 178°–179° C. Yield: 80%.

A number of compounds within the present invention and other compounds, including the compounds of de Stevens U.S. Pat. No. 3,211,735, col. 11–12. Compounds 2 and 12 were tested for antiaggressive activity and also for hypnotic activity.

The antiaggressive activity was carried out using the fighting test (mouse) according to the method of R. E. Tedeschi and co-workers, J. Pharmacol. Exp. Therap. Vol. 125, page 28 (1959).

In this method grown male mice, in every case in pairs, were placed in a cage with a latticework bottom of about 13×13 cm and were irritated through the bottom with an electric current for 3 minutes whereupon the two mice took on a specific characteristic combat position (the two mice oriented themselves in opposition and looked at each other; occasionally they even attached).

The typical fighting behavior of the mice can be eliminated by antiaggressive materials.

Then the ED 50 was ascertained from a large number of mice pairs by probability analysis. The ED 50 is that dosage at which in 50% of the mice pairs investigated there remained the typical combat position.

In following Table 2 the antiaggressive activity of the compounds is expressed by the ED 50.

The determination of the hypnotic activity by means of the hexobarbital (Evipan) potentiation test was carried out relying on the process of G. Osterloh et al., Arzneimittel Forschung, Vol. 16, pages 901–910 (1966).

There were injected intraperitoneally into mice 35 mg/kg of hexobarbital sodium in the form of a solution (35 mg in 10 ml of solution). The dosage was so chosen that the control animals (receiving only hexobarbital and gum tragacanth) did not sleep. One hour before giving the barbiturate the test substance was dispensed orally. The test substance in each case were suspended in gum tragacanth (0.75% solution in dimeralized water) and applied orally, using 0.3 ml of this solution per grams of mouse. Then there was recorded every five minutes for one hour the number of the sleeping animals in the individual groups. The number of the sleeping animals expressed in percent of the number of animals in the group gives the effect of the test substance in regard to the strengthening of the effect of the barbiturate. This value was entered in a coordinate system (ordinate: effect in %, abscissa: time of the reading) and the time curve drawn for the individual dosages.

To determine the activity there were planimetered the surfaces defined by the individual time curves against the abscissa or the curve of the control group and recalculated in percent of total surface (=maximum possible effect). The thus ascertained percent numbers give the effect of the individual dosages of the test substances over the entire duration of the test and permit the plotting in a probability system closure-effectiveness—lines and to revel off an ED 50.

There were employed fasting female NMRI mice of the research animal breed Ivanovas/Kisslegg weighing 18–22 grams. As food there was used Altromin R. The mice were kept at room temperature in Makrolon containers size III.

The results in the tests are also set forth in Table 2. Furthermore there is set forth in Table 2 the quotient $$\frac{ED\ 50/Hexobarbital\ Test}{ED\ 50/Combat\ Test}$$

It is important that this quotient be greater than 1 because otherwise any antiaggressive activity is overruled by the hypnotic activity. Table 2 of this Declaration shows that all of the compounds within the presently disclosed invention had a quotient well above 1 while the two compounds of de Stevens had a quotient below 1. The table further shows that all of the compounds tested which are within claims had a quotient well above that of the commercial drugs Diazepam and chlordiazepoxide. The compound of Example 17 also had a quotient well above that of the commercial drugs while the compound of Examples 10, 12 and 13 had a quotient in the same ball park as that of diazepam.

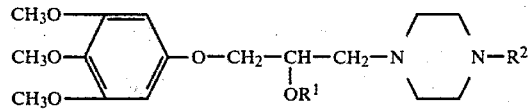

in which $R^1$ is hydrogen atom or $C_2$ to $C_6$-alkanoyl group, and $R^2$ represents phenyl substituted by the groups $R^3$ and $R^4$, the $R^3$ and $R^4$ each representing hydrogen, hydroxyl, $C_1$ to $C_6$-alkanoxy group, $C_2$ to $C_6$-alkanoyloxy group, amino group or $C_2$-$C_6$-alkanoylamino group with proviso at least one of $R_3$ and $R_4$ is not hydrogen and their salts.

2. A compound according to claim 1 in the form of the free base.

3. A compound according to claim 1 in the form of a pharmaceutically acceptable acid addition salt.

4. A compound according to claim 1 wherein $R^3$ and $R^4$ substituents are in the ortho and para positions.

5. A compound according to claim 1 wherein $R^3$ is hydrogen and $R^4$ is other than hydrogen.

6. A compound according to claim 1 wherein $R^1$ is hydrogen.

7. A compound according to claim 6 wherein $R^3$ is hydrogen.

8. A compound according to claim 7 wherein $R^4$ is $C_1$ to $C_4$ alkoxy.

9. A compound according to claim 8 wherein $R^4$ is $C_1$ to $C_6$ alkoxy.

10. A compound according to claim 9 wherein $R^4$ is methoxy.

11. A compound according to claim 10 wherein $R^4$ is 2-methoxy.

12. A compound according to claim 10 wherein $R^4$ is 3-methoxy.

13. A compound according to claim 7 wherein $R^4$ is hydroxy.

14. A compound according to claim 13 wherein $R^4$ is

TABLE 2

| Example No. | D-Number | Ed 50 mg/kg per os Combat Test | Hexobarbital Test | ED 50/Hexobarbital Test ED 50/Combat Test |
|---|---|---|---|---|
| 1 | 13 112 | 1.4 | 77 | 55 |
| 7 | 13 098 | 5.5 | 71 | 13 |
| 20 | 14 342 | 1.3 | 93 | 71 |
| 24 | 14 417 | 3.3 | 355 | 107 |
| 25 | 14 192 | 1.4 | 145 | 103 |
| 30 | 14 841 | 3.2 | 96 | 30 |
| 31 | 14 964 | 3.8 | 59 | 15.5 |
| 10 | 13 615 | 14 | 50 | 3.6 |
| 12 | 13 324 | 12 | 41 | 3.4 |
| 13 | 13 211 | 13 | 47 | 3.6 |
| 17 | 13 114 | 9 | 150 | 16.6 |
| de Stevens (2nd compound col. 12) | 14 911 | 42 | 2.75 | 0.06 |
| de Stevens (12th compound col. 12) | 14 919 | 51 | 3.25 | 0.06 |
| | Diazepam | 1.4 | 5.1 | 3.6 |
| | Chlordiazepoxid | 6.4 | 41 | 6.4 |

2-hydroxy.

15. A compound according to claim 7 wherein $R^4$ is $C_2$-$C_6$-alkanoylamino.

16. A compound according to claim 15 wherein $R^4$ is acetamido.

17. A compound according to claim 16 wherein $R^4$ is 2-acetamido.

What is claimed is:

1. A compound corresponding to the formula

18. A compound according to claim 7 wherein $R^4$ is amino.

19. A compound according to claim 18 wherein $R^4$ is 2-amino.

20. A compound according to claim 7 wherein $R^4$ is $C_2$ to $C_6$ alkanoyloxy.

21. A compound according to claim 20 wherein $R^4$ is acetoxy.

22. A compound according to claim 21 wherein $R^4$ is 2-acetoxy.

23. A compound according to claim 1 where $R^1$ is $C_2$ to $C_6$-alkanoyloxy.

24. A compound according to claim 23 where $R^1$ is acetyl.

25. A compound according to claim 24 wherein $R^3$ is hydrogen.

26. A compound according to claim 25 wherein $R^4$ is $C_1$ to $C_6$ alkoxy.

27. A compound according to claim 26 where $R^4$ is methoxy.

28. A compound according to claim 27 where $R^4$ is 2-methoxy.

29. A medicament containing as an active ingredient in an amount sufficient to exert a tranquilizing effect a compound of claim 1 together with a pharmaceutical excipient.

30. A method of imparting a neuroleptic or tranquilizing effect in a mammal comprising administering to the mammal an amount of a compound of claim 1 sufficient to cause said effect.

31. A method according to claim 30 wherein the compound is administered orally.

32. A method according to claim 31 wherein there is administered orally at least 0.1 mg/kg body weight of the mammal.

33. A method according to claim 30 wherein the compound is administered intravenously.

34. A method according to claim 33 wherein there is administered intravenously at least 0.01 mg/kg body weight of the mammal.

35. A method according to claim 30 wherein $R^1$ is hydrogen, $R^3$ is hydrogen and $R^4$ is 2-methoxy, 3-methoxy, 2-hydroxy, 2-acetamido, 2-amino or 2-acetoxy or $R^1$ is acetyl, $R^3$ is hydrogen and $R^4$ is 2-methoxy.

36. A method according to claim 35 wherein $R^1$ is hydrogen.

37. A method according to claim 36 where $R^4$ is 2-methoxy.

38. A method according to claim 36 where $R^4$ is 2-hydroxy.

39. A method according to claim 38 where $R^4$ is 2-acetamido.

40. A method according to claim 36 where $R^4$ is 2-amino.

41. A method according to claim 36 where $R^4$ is 2-acetoxy.

42. A method according to claim 36 where $R^4$ is 3-methoxy.

43. A method according to claim 35 wherein $R^1$ is acetyl, $R^3$ is hydrogen and $R^4$ is 2-methoxy.

* * * * *